United States Patent [19]
Pohjola

[11] Patent Number: 5,224,405
[45] Date of Patent: Jul. 6, 1993

[54] PROCESS FOR ROTATING AND PLACING A STRIP OF MATERIAL ON A SUBSTRATE

[75] Inventor: Dale A. Pohjola, Appleton, Wis.

[73] Assignee: Kimberly-Clark Corporation, Neenah, Wis.

[21] Appl. No.: 975,145

[22] Filed: Nov. 12, 1992

Related U.S. Application Data

[60] Continuation of Ser. No. 827,237, Jan. 29, 1992, abandoned, which is a division of Ser. No. 504,411, Apr. 6, 1990, Pat. No. 5,104,116.

[51] Int. Cl.⁵ .............................................. B32B 31/00
[52] U.S. Cl. ................................... 83/24; 83/152; 83/154; 156/519; 198/377; 271/185
[58] Field of Search ............... 271/185; 198/377, 378; 156/519; 83/152, 154, 100, 23, 24

[56] References Cited

U.S. PATENT DOCUMENTS

| | | | |
|---|---|---|---|
| Re. 33,063 | 9/1989 | Obeda | 156/73.1 |
| 3,728,191 | 4/1973 | Wierzba et al. | 156/265 |
| 3,828,367 | 8/1974 | Bourgeois | 2/224 |
| 4,242,167 | 12/1980 | Hoffmann | 156/357 |
| 4,285,747 | 8/1981 | Rega | 156/164 |
| 4,394,898 | 7/1983 | Campbell | 198/374 |
| 4,394,933 | 7/1983 | Ackley | 221/173 |
| 4,608,115 | 8/1986 | Schroth et al. | 156/519 |

Primary Examiner—Douglas D. Watts
Assistant Examiner—Kenneth E. Peterson
Attorney, Agent, or Firm—Douglas L. Miller

[57] ABSTRACT

An apparatus and process for receiving and rotating a strip of material toward a continuously moving surface, and then orienting the strip of material so that it is surfacely placed generally flat with the continuously moving surface.

4 Claims, 6 Drawing Sheets

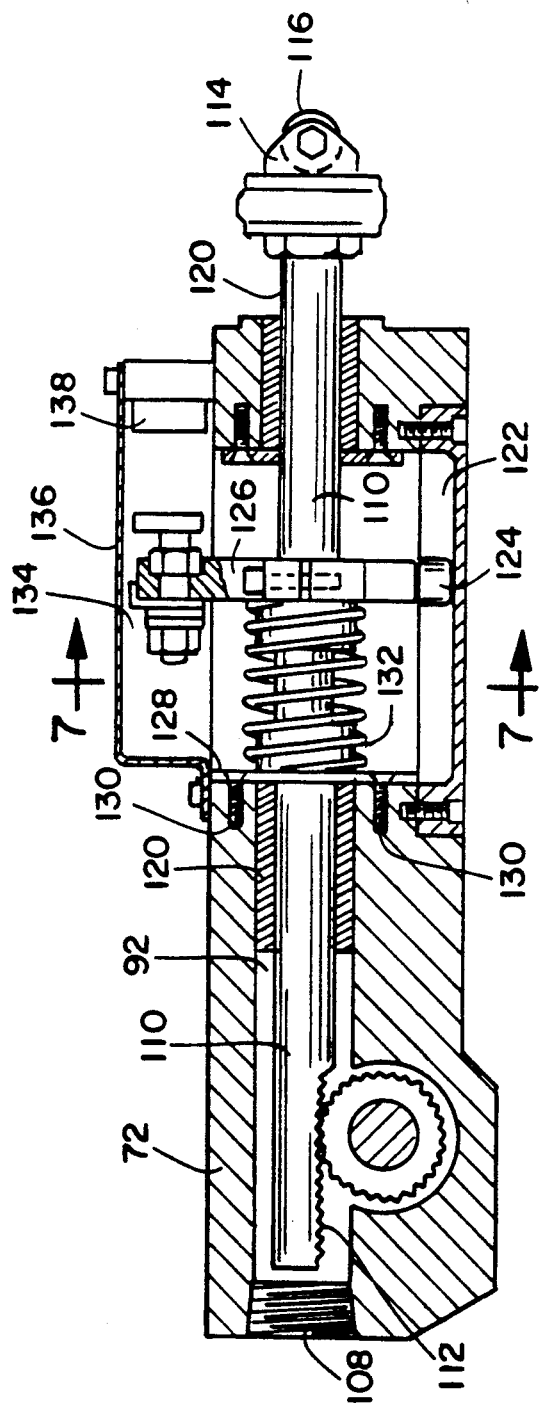
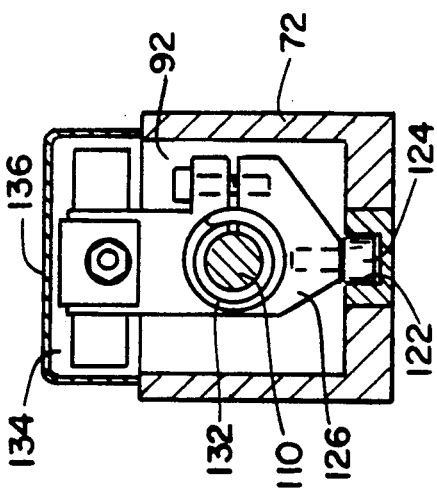

PROCESS FOR ROTATING AND PLACING A STRIP OF MATERIAL ON A SUBSTRATE

This is a continuation of copending application Ser. No. 07/827,237 filed on Jan. 29, 1992, now abandoned which is a division of Ser. No. 07/504,411 filed on Apr. 6, 1990, now U.S. Pat. No. 5,104,116.

BACKGROUND OF THE INVENTION

The present invention relates to an apparatus and process for receiving and rotating strips of material on a transfer roll toward a moving surface and transferring the strips to the moving surface. More specifically, the present invention relates to cutting discrete strips of continuously moving material, rotating the strips, and then surfacely placing the strips with the continuously moving surface.

Various apparatus are currently available that receive strips of cut material and then manipulate the material by rotating or pivoting the material relative to its initial direction of movement and then placing it on or near a continuously moving surface. In placing the strips of material with the moving surface, the apparatus generally begin the placement by initially contacting the leading edge of the strip with the moving surface and then progressively laying or rolling the strip upon the surface with the trailing edge of the strip being the last to be laid upon the moving surface.

A problem that exists with these apparatus is that the rotation of the transferring element, upon which the strip is carried, can cause the transferring element to bite or dig into the moving surface, thereby undesirably cutting or otherwise mutilating the moving surface. For example, as the transferring element releases the leading edge of the strip material and then begins to pivot or rotate upwardly away from the moving surface, the trailing edge of the transferring element pivots or rotates against and into the moving surface. This can damage the moving surface and/or disrupt the proper positioning or registration of the strip with the moving surface, and is particularly undesirable when the moving surface is a woven or non-woven material.

This problem is particularly acute when the strip being laid upon the moving surface is of a generally elongate or rectangular shape having its longest axis parallel to the direction of movement of the moving surface.

Another problem occurs in properly releasing the strip of material from the transferring element to the moving surface. Generally, these strips of material are held on their respective transferring elements by a vacuum effect created through perforations or holes in the outer surface of the transferring element. The problem is that these apparatus may not extinguish the vacuum against the strip of material as the strip of material is progressively transferred leading edge to trailing edge on the moving surface. For example, if the vacuum is not progressively extinguished as the strip is progressively laid from the transferring element to the surface, portions of the strip element can continue to be held by vacuum against the transferring element resulting in an undesirable pleat or fold in the strip material, skewed alignment of the strip material with the moving surface, and the like.

SUMMARY OF THE INVENTION

In one form of the present invention, there is provided a process for rotating and surfacely placing a strip of material with a moving surface element. The process generally comprises the steps of moving in a first direction a surface element, providing a strip of material having a first axis in a first angular orientation to the first direction of movement, rotating the strip of material to a second angular orientation to the first direction of movement, and then surfacely placing the strip of material generally flat with the surface element.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein:

FIG. 6 is a sectional view of FIG. 4 taken along line 6—6 and viewed in the direction of the arrows; and FIG. 7 is a sectional view of FIG. 6 taken along line 7—7 and viewed in the direction of the arrows.

DESCRIPTION OF A PREFERRED EMBODIMENT

Figure 1:
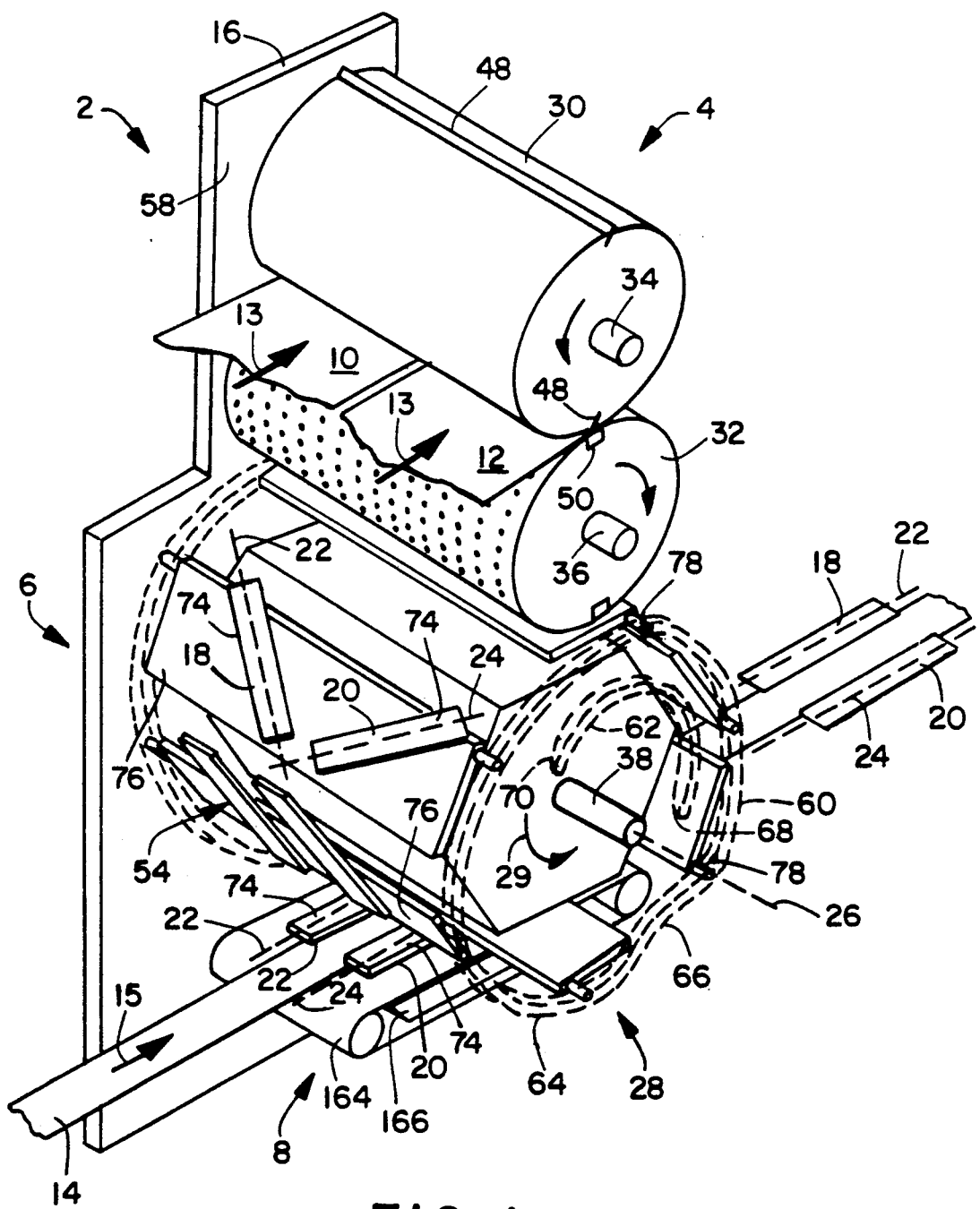
FIG. 1 is a partially broken away perspective view of a preferred embodiment of the present invention.
Figure 2:
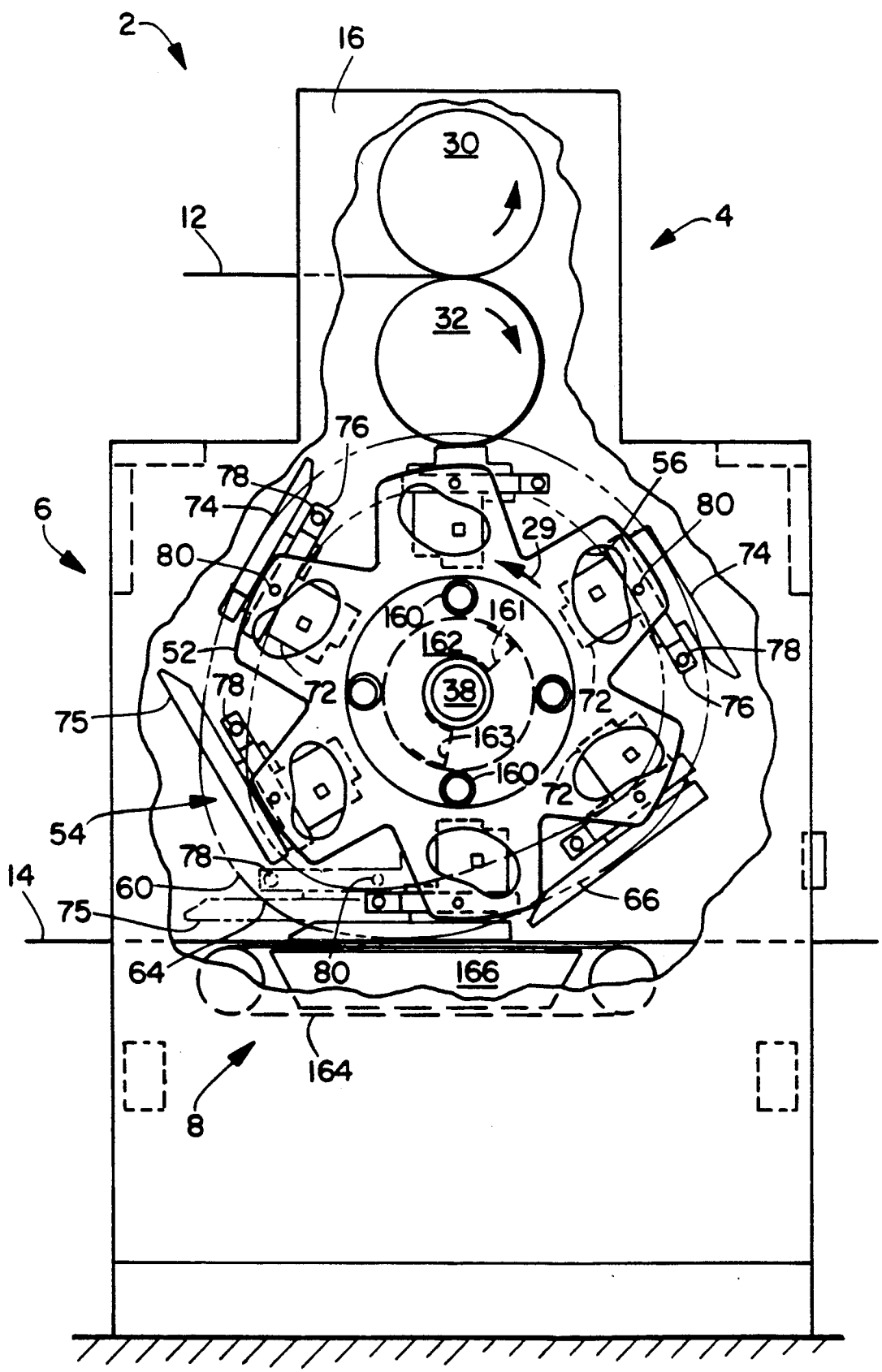
FIG. 2 is a partially broken away side elevational view of the embodiment in FIG. 1.
Figure 3:
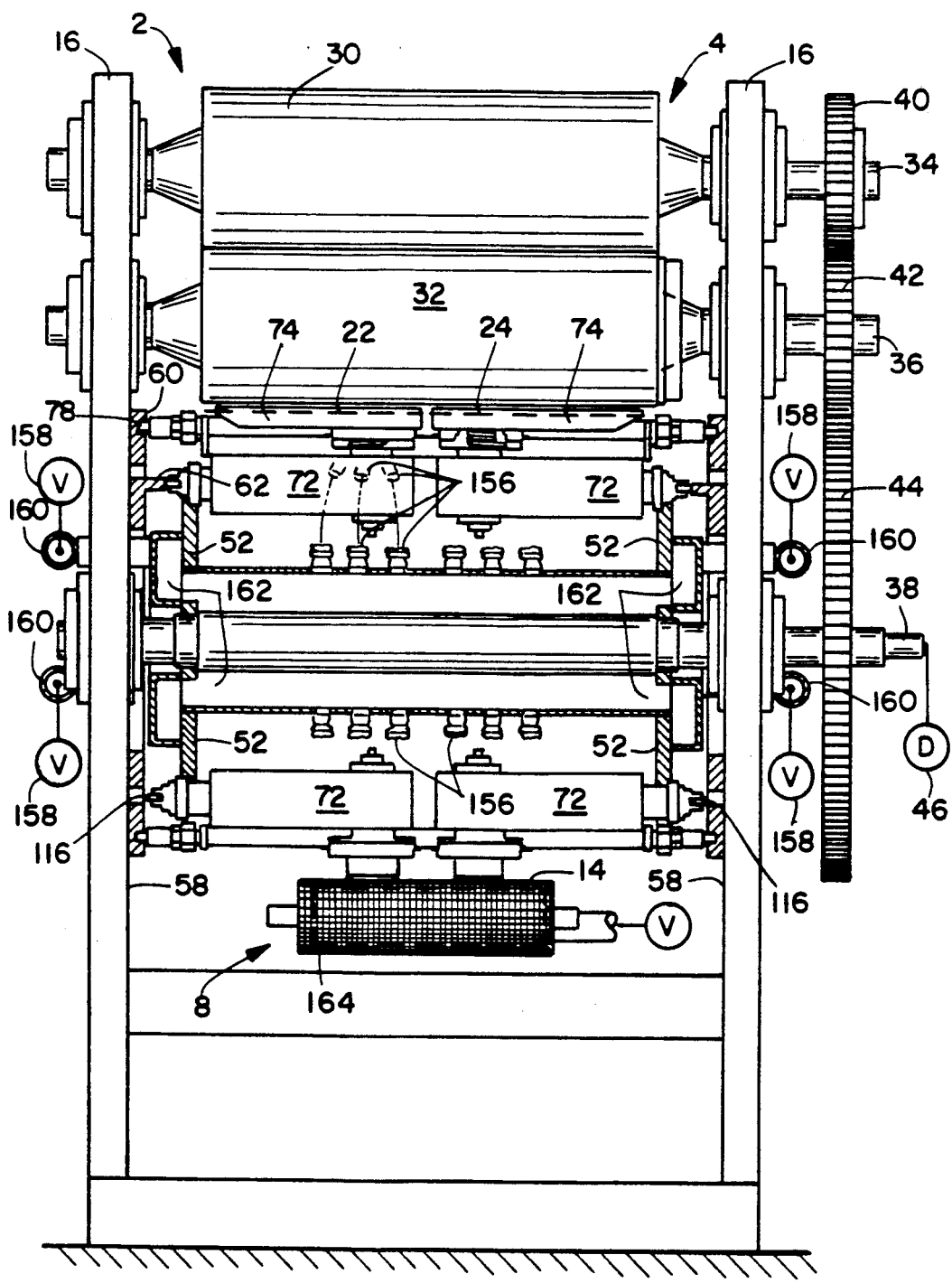
FIG. 3 is a front elevational view partially broken away and cross-sectioned of the embodiment in FIG. 1.

Referring to FIGS. 1-3, there is illustrated an apparatus 2 which may be operated according to the principles of the present invention. Apparatus 2 generally comprises cutting assembly 4, handling assembly 6, and conveyor assembly 8. A pair of continuous webs 10,12 are supplied to cutting assembly 4 from any suitable web supply assembly (not shown). One such suitable assembly is that described in U.S. Pat. No. 4,608,115 issued on Aug. 26, 1986, to the assignee of the present invention, and which is incorporated by reference herein. Webs 10, 12 can be any type of material such as a woven or nonwoven material, and can be supplied as a single web or ribbon of material, or a plurality of webs or ribbons of material. If there is a plurality of webs or ribbons of material, the materials of which the webs or ribbons are made can also be different. Examples of nonwoven webs include, but are not limited to, paper and paper-like material, pressure-sensitive tape material, mechanical fastener material such as hook-and-loop material, films of thermoplastic material, a spunbond or meltblown thermoplastic material, an elastomeric material, or a stretch-bonded laminate material. A stretch-bonded laminate material comprises a stretchable material that is stretched and then bonded to a gatherable material and then allowed to relax to form the laminate.

Conveyor assembly 8 has a continuous substrate 14 delivered thereto from any conventional type of supply assembly, such as one described in the aforementioned U.S. Pat. No. Substrate 14 can be any type of woven or nonwoven material. Although webs 10, 12 and substrate 14 have been described as continuous materials, the present invention also contemplates that substrate 14 can be a series of discrete material sheets and that webs 10, 12 can be supplied to handling assembly 6 as discrete strips or ribbons of material.

The illustrated embodiment of the present invention is being used to cut web 10 and web 12 into discrete pieces of web material, such as web strip 18 and web strip 20, respectively (FIG. 1). Webs 10, 12 are cut such that longitudinal axis 22 of web strip 18 and longitudinal axis 24 of web strip 20 are generally parallel to roll axis 26 of transfer roll 28 in handling assembly 6. The present invention is utilized in this embodiment to rotate cut web strips 18, 20 90° relative to the direction of movement of substrate 14 as indicated by arrow 15, and then to dispose web strip 18 and web strip 20 with substrate 14 such that axes 22, 24 of web strips 18, 20 are generally parallel to the direction of movement of continuous substrate 14. It should be understood that before web strips 18, 20 are rotated 90°, their respective axes 22, 24 are generally in axial alignment.

The present invention also contemplates that axes 22, 24 may be cut at any desired first angular orientation, such as 45°, relative to roll axis 26, and then rotated to any desired second angular orientation, such as 135°, relative to axis 26.

Continuing to refer to FIGS. 1-3, cutting assembly 4 includes rotatable knife roll 30 and rotatable vacuum anvil roll 32, and handling assembly 6 includes rotatable transfer roll 28, all of which rolls are journaled between side frames 16 (FIG. 3). Transfer roll 28 is driven by a suitable drive system 46 connected to drive shaft 38 on which is fixed for rotation transfer roll gear 44. Knife roll 30 is driven by drive shaft 34 having fixed for rotation thereon knife gear 40, and vacuum anvil roll 32 is driven by drive shaft 36 having fixed thereon anvil gear 42. Upon operation of drive system 46, drive shaft 38 is rotated to cause rotation of transfer roll 28 and transfer roll gear 44 which is in meshing engagement with anvil gear 42. Anvil gear 42 rotates drive shaft 36 which in turn rotates anvil roll 32. Anvil gear 42 is in meshing engagement with knife gear 40 to rotate drive shaft 32 which in turn rotates knife roll 30. By varying the diameters of gears 40, 42, and 44, the rotational speeds of knife roll 30 and anvil roll 32 can be varied relative to each other and to transfer roll 28 as desired. Vacuum anvil roll 32 has a plurality of perforations therethrough, and a vacuum is provided within anvil roll 30 in any suitable manner, such as providing the vacuum through drive shaft 36 or in a similar manner as will be described hereafter with reference to transfer roll 28.

Knife roll 30 includes at least one knife blade 48 and anvil roll 32 includes at least one blade cutting surface 50 for cutting webs 10, 12 into respective web strips 18, 20. Generally, the number of blades 48 and cutting surfaces 50 will depend upon the desired length into which webs 10, 12 are to be cut. In this particular example, webs 10, 12 will be cut into lengths, as measured in the direction of movement of webs 10, 12 illustrated by arrows 13 in FIG. 1, that are shorter in dimension than the width of webs 10, 12, as measured in a direction 90° to the relative movement of webs 10, 12. Thus, when web strips 18, 20 are carried to and rotated 90° by handling assembly 6, the width dimension just described includes longitudinal axes 22, 24. Although not illustrated, the vacuum created within anvil roll 32 is extinguished just prior to or when anvil roll 32 rotates a pair of cut web strips 18, 20 to transfer roll 28 so that web strips 18, 20 will be transferred from anvil roll 32 to transfer roll 28 as explained hereafter.

Referring to FIGS. 2, 3, handling assembly 6 further includes a pair of side plates 52 secured to transfer roll 28 for rotation therewith. A plurality of puck assemblies 54 are disposed between the side plates 52 for receiving web strips 18, 20 from cutting assembly 4 and for rotating and transferring them to substrate 14. Side plates 52 have a plurality of cut-outs 56 to provide clearance for the movement of respective puck assemblies 54.

Figure 4:
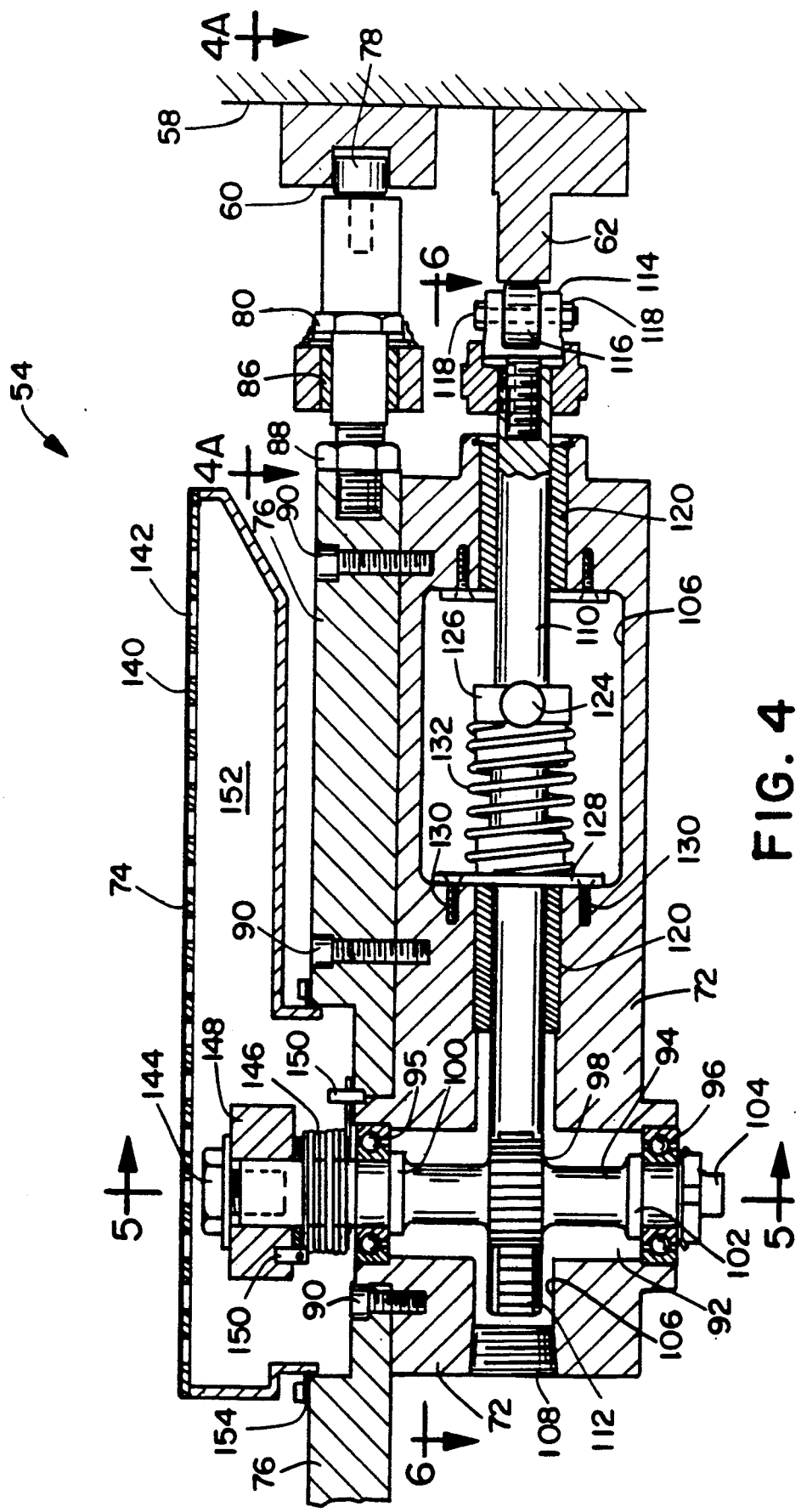
FIG. 4 is a cross-sectional view of a puck assembly for the embodiment in FIG. 1.

Referring to FIGS. 1-4A, side frames 16 have mutually facing and spaced apart inner walls 58, each of which has disposed thereon a closed-loop plate cam track or groove 60 and a barrel cam track or shoulder 62 disposed within the periphery of cam track 60. The two plate cam tracks 60 are identical in their path or cam track geometry and are identically disposed relative to roll axis 26. Similarly, both barrel cam tracks 62 are identical in track geometry and in placement relative to roll axis 26. Since both plate cam tracks 60 are identical and both barrel cam tracks 62 are identical, a description of a single cam track 60 and a single cam track 62 only will be made. Plate cam track 60 is a closed-loop with the eccentric or non-circular shape or form as illustrated in FIG. 2. Cam track 60 has a noticeably outwardly bowing or convex portion 64 and downstream thereof in the direction of rotation of transfer roll 28 a noticeably inwardly bowed or concave portion 66, which determine in part movement of each puck assembly 54. Each barrel cam track 62 is disposed within its respective plate cam track 60 and is oriented generally between about the 10 o'clock position and 4 o'clock position as illustrated in FIG. 1. Referring specifically to FIG. 4, it can be seen that plate cam track 60 is of a groove-like design, and that barrel cam track 62 is of a shoulder-type design. Referring now to FIG. 1, the ends of each barrel cam track 62 slope downwardly or taper inwardly toward inner wall 58 to form upstream slope 68 and downstream slope 70. The terms "upstream" and "downstream" are to be interpreted relative to the direction of rotation of transfer roll 28 as indicated by arrow 29. Thus, slope 70 is downstream from slope 68 in the direction of rotation of transfer roll 28.

Referring now primarily to FIGS. 4-7, a description of a single puck assembly 54 will be made, and it should be understood that the present invention contemplates either a single or multiple puck assemblies 54 disposed with handling assembly 6. Within the context of the present disclosure, the terms "dispose", "disposed on", "disposed with", and any variations thereof, are intended to mean as a minimum that one element can be formed integrally from another element, or one element can be separate structure joined to or operably connected to or placed with or near another element. Since each puck assembly in the present embodiment is identical, a description of a single puck assembly 54 only will be made. Puck assembly 54 generally comprises actuator box 72, a generally rectangular puck 74, and pivot plate 76. Actuator box 72 and puck 74 pivot with pivot plate 76, and puck 74 pivots or rotates about 90° relative to the pivot axis of pivot plate 76. For ease of understanding, the longest axes of pucks 74 will be identified and illustrated the same as the axes 22, 24 of strips 18, 20. Thus, FIG. 1 illustrates axes 22, 24 as axes for strips 18, 20, and also illustrates or represents the axes for pucks 74 shown in FIG. 3.

Figure 4A:
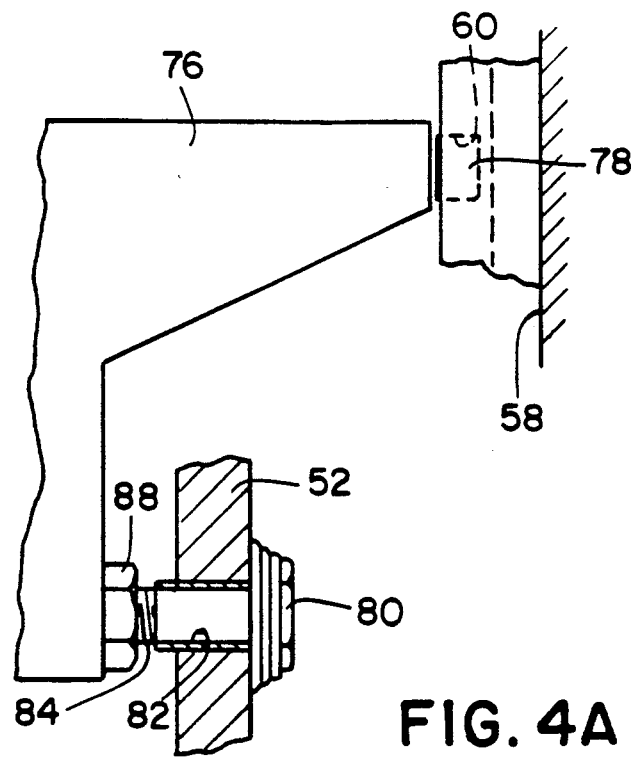
FIG. 4A is a sectional view of FIG. 4 taken along line 4A—4A and viewed in the direction of the arrows.

Referring now to FIGS. 1, 4, 4A, pivot plate 76 has a plate cam follower 78 rotatably mounted in its end and is movably or slidably disposed within plate cam track 60. Pivot plate 76 is pivotably mounted between side plates 52 by means of pivot bolts 80 (FIG. 4A) rotatably mounted within openings 82. The remote or free end portion of pivot bolt 80 has a threaded surface 84 threadedly received in pivot plate 76. Bearing assembly 86 (FIG. 4) is disposed between pivot bolt 80 and side plate 52 in opening 82, and jam nut 88 permits lateral or transverse displacement of pivot plate 76 between side plates 52. Although FIG. 4A shows only a single pivot bolt 80, opening 82, threaded surface 84, and jam nut 88, there are identical elements on the opposite end of pivot plate 76 so that it can pivot between side plates 52 about pivot bolts 80 as plate cam followers 78 move along plate cam tracks 60.

Referring now to FIGS. 4, 5, 6, and 7, actuator box 72 is threadedly secured to pivot plate 76 by a plurality of screws 90 so that actuator box 72 moves with pivot plate 76. Actuator box 72 includes a cavity 92 that has pinion shaft 94 rotatably mounted therein between bearing races 95, 96. As will be explained later, pinion shaft 94 extends outwardly from cavity 92 and upwardly through bearing race 95 as viewed in FIG. 4. Pinion shaft 94 also includes pinion gear 98 positioned between a pair of pinion flanges 100, 102 that are rotatably mounted against respective bearing races 95, 96. Pivot bolt 104 is threadedly engaged in the remote end of pinion shaft 94 as illustrated in FIG. 4 and with flanges 100, 102 serves to maintain pinion shaft 94 within cavity 92.

Referring specifically now to FIGS. 4 and 6, actuator box 72 has a passage 106 with one end stopped by removable plug 108. Linear actuator shaft 110 is slidably mounted within passage 106 and has disposed on its end near plug 108 rack gear 112 in meshing engagement with pinion gear 98 and on its opposite end that extends outwardly through actuator box 72 a yoke 114 that has rotatably mounted therewith barrel cam follower 116 that rides along barrel cam track or shoulder 62. Barrel cam follower 116 is rotatably mounted in yoke 114 by screw 118. Linear bearings 120 provide a good lubricating surface for the sliding motion of linear actuating shaft 110 and also maintain shaft 110 within passage 106. In order to prevent linear actuating shaft 110 from rotating within passage 106, shaft cam follower 124 is secured to linear actuating shaft 110 and slidably moves along shaft cam track 122 in actuating box 72 (FIG. 7). Shaft cam follower 124 is rotatably secured to stop plate 126 that is secured on linear actuating shaft 110. Plate 128 is disposed within passage 106 and secured to actuator box 72 in any suitable manner, such as with screws 130. Compression spring 132 is mounted on shaft 110 and between plate 128 and stop plate 126 so as to urge linear actuating shaft 110 and its barrel cam follower 116 against barrel cam track 62 (FIG. 4). As transfer roll 28 rotates causing barrel cam follower 116 to move along barrel cam track 62 and then along downstream slope 70, compression spring 132 urges cam follower 116 down slope 70 to move linear actuating shaft 110 in a left-to-right direction toward inner wall 58 as viewed in FIG. 4. The end of stop plate 126 opposite shaft cam follower 124 extends upwardly into compartment 134 formed by cover 136 attached in any suitable manner to actuating box 72. Dampening device 138, which can be any suitable device such as a rubber material, is secured to cover 136 or any suitable nearby structure and dampens any linear vibrations caused by compression spring 132 acting on linear actuator shaft 110.

Figure 5:
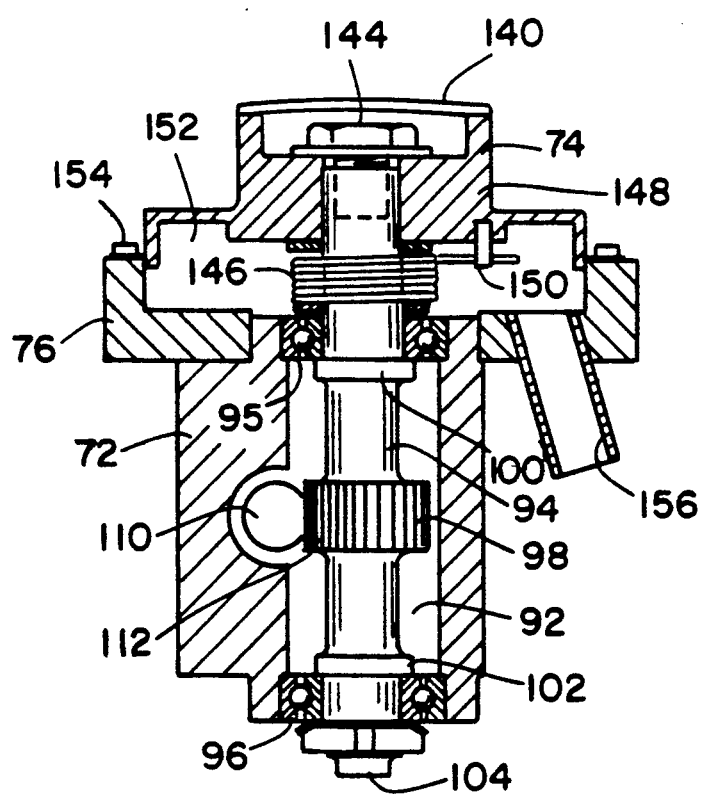
FIG. 5 is a sectional view of FIG. 4 taken along line 5—5 and viewed in the direction of the arrows.

Referring primarily to FIGS. 4 and 5, puck 74 has puck cover 140 with a plurality of vacuum ports 142 disposed therein. Puck 74 is secured to pinion shaft 94 by means of bolt 144 and pivots or rotates with pinion shaft 94. Torsion spring 146 is received on pinion shaft 94 between puck hub 148 and bearing race 95. Spring support pins 150 securely fix ends of torsion spring 146 to puck hub 148 and actuator box 72. Torsion spring 146 serves to minimize or eliminate backlash caused by pinion gear 98 and rack gear 112 of shaft 110. Puck cover 140 and actuator box 72 form vacuum chamber 152 that communicates with the outside atmosphere through vacuum ports 142. Felt seal 154 maintains the vacuum between puck 74 and actuator box 72. Vacuum passage 156 (FIG. 5) communicates with and provides a vacuum within vacuum chamber 152, and will be explained in greater detail below.

Referring now to FIGS. 2, 3, and 5, an explanation of the vacuum system for handling assembly 6 will be made. Vacuum source 158 creates a vacuum through vacuum lines 160 and within vacuum shoes 162. The vacuum passages 156 are in fluid communication with vacuum shoe 162 and vacuum chamber 152 (FIG. 5) to create a vacuum within chamber 152 that operates through vacuum ports 142 (FIG. 4). As illustrated in FIG. 2, vacuum shoe 162 is operative to provide a vacuum in chamber 152 and through ports 142 in a counter-clockwise direction from about the 2 o'clock position to about the 6 o'clock position during rotational travel of puck assemblies 54. This permits web strips 18, 20 to be fluidly adhered to respective pucks 74 and then released at the appropriate time onto conveyor assembly 8. Shoe end walls 161, 163 (FIG. 2) block-off the vacuum effect from vacuum source 158 to extinguish the vacuum within pucks 74. The vacuum effect can also be extinguished by a blast of air being delivered into chamber 152 by any suitable fluid-delivery mechanism.

Conveyor assembly 8 can be of a conventional type comprising a driven endless conveyor belt 164 having a surface that permits the vacuum created by vacuum box 166 to act therethrough and against the bottom surfaces of web strips 18, 20 to hold them in a predetermined position relative to or with substrate 14. If strips 18, 20 are placed directly on top of and within the periphery or longitudinal edges of substrate 14, then strips 18, 20 or substrate 14 can be provided with an adhesive means to maintain strips 18, 20 in place.

In operation of this specific embodiment of the present invention, continuous webs 10, 12 are delivered in parallel to cutting assembly 4 to be cut by blade 48 on cutting surface 50. The cut web strips 18, 20 are maintained on anvil roll 32 by means of the created vacuum and are then transferred to their respective pucks 74. Transfer roll 28 then rotates and in doing so plate cam follower 78 moves along the closed-loop path of plate cam track 60 to pivot pivot plate 76 about pivot bolt 80 (FIG. 2). As barrel cam follower 116 approaches the upstream slope 68 of barrel cam track 62 and moves therealong, linear actuating shaft 110 is moved in a right-to-left direction as viewed in FIG. 4 so that rack gear 112 moves in meshing engagement with pinion gear 98 to rotate pinion shaft 94. As pinion shaft 94 pivots, puck 74 is pivoted as illustrated in FIG. 1 in order to align puck axes 22, 24 with the direction of movement of substrate 14 and generally perpendicular to roll axis 26. With reference to FIG. 2, it is important to the present invention that each puck 74 be pivoted or moved by plate cam follower 78 in plate cam track 60 so that the outwardly facing surface 75 of each puck 74 carrying its respective web strip is generally parallel with the surface of substrate 14 just prior to contacting substrate 14 as illustrated in FIG. 2. As transfer roll 28 continues to rotate, plate cam follower 78 moves through convex portion 64 of plate cam track 60 to pivot puck 74 so that puck surface 75 is surfacely placed flat against or with substrate 14 as desired. The term "surfacely placed" and variations thereof means that the generally flat surface area of puck 74 and the surface of substrate 14 are brought or placed simultaneously together in one movement, as opposed to, for example, bringing the leading edge of puck surface 75 first into contact with substrate 14 and then progressively laying or rolling-down the remainder of puck surface 75 on substrate 14. As transfer roll 28 moves counter-clockwise from about the 7 o'clock position to the 6 o'clock position as viewed in FIG. 2, the respective web strip is surfacely placed in a flat manner upon or relative with substrate 14 and then held there through about the 6 o'clock position due to the subsequent travel of plate cam follower 78 from convex portion 64 to concave portion 66 of cam track 60. Near about the 6 o'clock position, the web strip is released from puck 74 upon extinguishment of the vacuum in puck 74 caused by shoe end wall 161 blocking-off the vacuum effect (FIG. 2). From this point on in the rotation of transfer roll 28, web strips 18, 20 have been positioned as desired relative to substrate 14; for example, web strips 18, 20 can be placed upon, adjacent to, or spaced from substrate 14, as desired. Pucks 74 are then surfacely lifted from substrate 14 and continue to rotate towards cutting assembly 4 to receive other web strips to be placed upon substrate 14. Web strips 18, 20 which are placed with substrate 14 are then conveyed by conveyor assembly 8 to another handling station for appropriate processing.

The present invention may also be adapted to place a plurality of strips 18, 20 with a multiple number of substrates 14 in a manner similar to that just described.

While this invention has been described as having a preferred embodiment, it will be understood that it is capable of further modifications: This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. A process for rotating and surfacely placing a strip of material with a surface element, comprising the steps of:

continuously moving in a first direction a surface element, continuously providing a material having a first axis in a first angular orientation to the first direction of movement, cutting a strip from the material, sequentially rotating the strip of material so that the first axis of the strip is in a second angular orientation to the first direction of movement, positioning the strip of material generally parallel to and spaced-apart from the surface element, and then, while maintaining the strip and the surface element generally parallel, moving the strip of material into generally flat contact with the surface element.

2. The process of claim 1 further comprising the step of maintaining the strip flat with the surface element for a predetermined length of travel.

3. The process of claim 1 wherein the step of moving the strip includes moving additional strips in a spaced-apart manner relative to each other onto the surface element.

4. The process of claim 3 wherein the step of providing includes providing continuously a plurality of materials, and wherein the step of moving the strips further includes moving the strips onto opposite sides of a plurality of surface elements.

* * * * *